United States Patent [19]
Bennwik et al.

[11] Patent Number: 5,709,659
[45] Date of Patent: Jan. 20, 1998

[54] NON-REUSABLE INJECTION DEVICE

[75] Inventors: Percy Bennwik, Saltsjö-Boo; Bo Eklund, Vällingby, both of Sweden

[73] Assignee: Pharmacia & Upjohn AB, Stockholm, Sweden

[21] Appl. No.: 722,207

[22] PCT Filed: Apr. 13, 1995

[86] PCT No.: PCT/SE95/00406

§ 371 Date: Oct. 15, 1996

§ 102(e) Date: Oct. 15, 1996

[87] PCT Pub. No.: WO95/28191

PCT Pub. Date: Oct. 26, 1995

[30] Foreign Application Priority Data

Apr. 14, 1994 [SE] Sweden ................................ 9401273

[51] Int. Cl.⁶ .................................................. A61M 5/00
[52] U.S. Cl. ........................... 604/110; 604/192; 604/193
[58] Field of Search ................................ 604/110, 187, 604/192, 193, 194, 218, 263

[56] References Cited

U.S. PATENT DOCUMENTS

| | | |
|---|---|---|
| 2,453,591 | 11/1948 | Poux . |
| 3,882,866 | 5/1975 | Zackheim . |
| 4,270,536 | 6/1981 | Lemelson ................... 604/110 |
| 4,710,170 | 12/1987 | Haber et al. ................ 604/110 |
| 4,917,243 | 4/1990 | Abrams et al. . |
| 4,919,652 | 4/1990 | Alter et al. ................. 604/110 |
| 4,944,397 | 7/1990 | Miller . |
| 5,004,460 | 4/1991 | Gimeno . |
| 5,267,976 | 12/1993 | Guerineau et al. . |
| 5,269,760 | 12/1993 | Bina . |
| 5,318,537 | 6/1994 | Van Der Merwe ........ 604/110 |

FOREIGN PATENT DOCUMENTS

| | | |
|---|---|---|
| 9209294 | 1/1992 | South Africa . |
| 2256146 | 4/1992 | United Kingdom . |
| WO89/08468 | 3/1989 | WIPO . |
| WO91/08786 | 12/1990 | WIPO . |
| WO92/12748 | 1/1991 | WIPO . |
| WO94/05356 | 8/1993 | WIPO . |

*Primary Examiner*—John D. Yasko
*Attorney, Agent, or Firm*—Lowe, Price, LeBlanc & Becker

[57] ABSTRACT

The present invention is directed to a drug containing non-reusable syringe having a hollow plunger rod provided with a rupture line for permanently detaching its rear part which can be engaged with the needle holder to perform a radial motion that breaks the needle which thereafter is received by a cavity in the rear part of the detached plunger rod. The rear part of the plunger rod can also be attached to the needle holder to protect the user from accidental needle sticks.

8 Claims, 2 Drawing Sheets

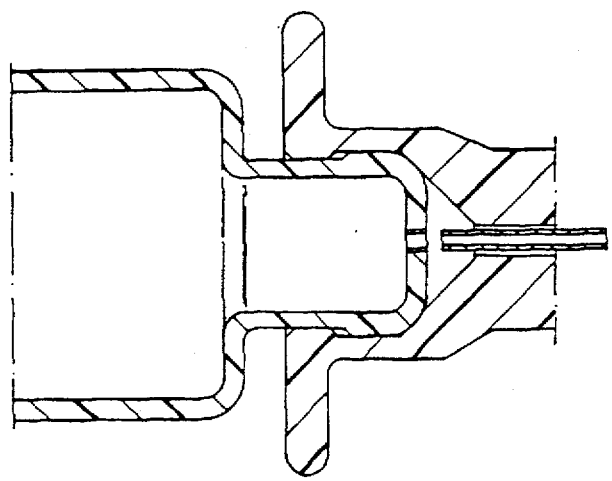
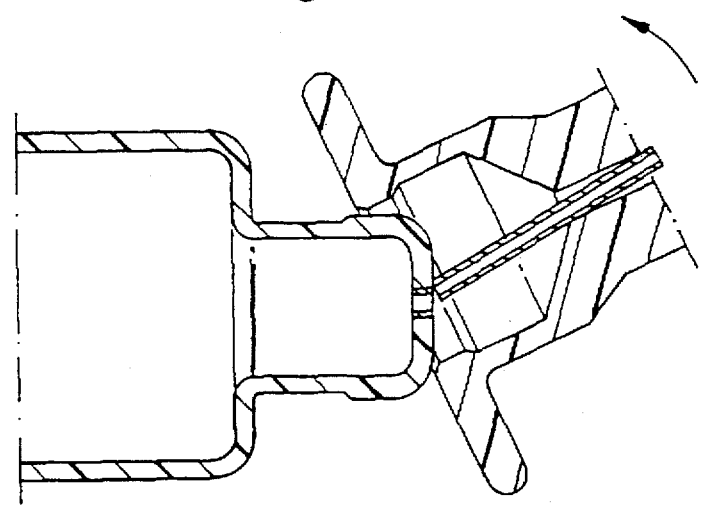
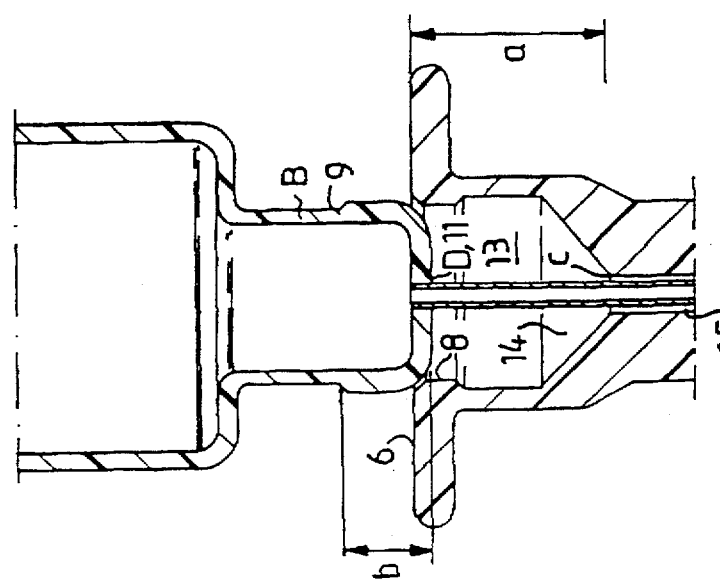

NON-REUSABLE INJECTION DEVICE

FIELD OF INVENTION

The present invention is related to a non-reusable syringe containing a single dosage of a drug. The syringe is of a conventional type and is provided with means for permanent destruction so it will be impossible to use repeatedly. It is also provided with a needle destruction device and a needle cover device to avoid accidental needle sticks.

BACKGROUND OF THE INVENTION

Many medical authorities request syringes that are easily and safely destroyable to prevent contaminated goods from being used and circulated without control. It is also highly desirable to protect the personnel handling the syringes from accidental sticks from used needles.

There are a plurality of devices described in the prior art that disclose irreversible or temporary needle retraction of the needle into the syringe barrel with locking means, see e.g. U.S. Pat. No. 5,267,976. The U.S. Pat. No. 5,269,760 discloses a single use syringe having its push rod locked into the syringe body when fully advanced after injection.

In the International patent Application WO 89/08468, it is disclosed how a part of the plunger rod of a syringe is detached and used as a temporary needle protector. In this syringe it is, however not, provided for means to destroy the needle, which means there is a risk it will be reused.

The South African patent specification ZA 9209204 and the corresponding British patent application GB 2 256 146 disclose syringes made non-reusable, having a needle receiver for disposed needles formed in a part of the syringe plunger. After administering the drug with this syringe, the hollow plunger rod is permanently broken from its piston when withdrawn from the syringe barrel. The broken hollow plunger rod will thereafter be used to demount the needle of the syringe and introduce it through an axially extended slot in its side wall. Finally, the broken plunger rod housing the needle is re-inserted into and locked to the syringe barrel. This type of syringe requires, however, a specially formed type of needle mounted to the syringe and also a specific syringe body with locking means in order to re-insert the broken plunger with the needle to protect the needle from being used inadvertently and protect the user from accidental sticks. These features will make the syringe complicated and costly to manufacture due its many specially designed parts. In daily hospital operative practice, by personnel often exposed to stressed situations, there is always a risk that the needle will not be correctly demounted or not removed at all by the broken plunger. Another risk with this type of syringe is that the broken plunger with detached syringe is not properly locked to syringe barrel or, in worst case, never re-inserted into the barrel, due to stress or neglectfulness of the user, which may lead to the needle being exposed for inadvertent use.

It would therefore be desirable to provide a disposable single use syringe which can minimize the exposure of the needle, and with a minimum of movements, safely can make both the needle and plunger mechanism entirely inoperative after use. It is also desirable to, at the highest possible extent, to use only standardized syringe components, to reduce manufacturing costs and increase the applicability.

The present invention intends to fulfil these requirements by providing a syringe to the largest possible extent consisting of a standardized components, having a permanently detachable hollow plunger rod which both can be used to break the needle and be used as housing for the broken needle when attached to the needle holder of the front part of the syringe. Such a syringe has a number of dear advantages in that:

- a separate needle breaker will not be necessary to employ for its destruction;
- the broken needle will immediately be placed in the hollow plunger rod without unnecessary exposure;
- the syringe may be safely used for self-administration in the home of the patient and be disposed with ordinary domestic refusals;
- the detached plunger rod can replace the protecting rubber shield after the injection;
- the syringe guarantee for safety during all steps of its handling and can thereby fulfil rigorous security provisions
- the needle will be effectively and simply made inoperative.

DESCRIPTION OF THE INVENTION

The present invention is directed to a drug containing non-reusable syringe having a movable, hollow plunger rod in connection with a plunger, for injecting the drug through the needle. The syringe has a cover attachable to the needle holder for protecting the needle after the injection, wherein the said plunger rod is provided with a rupture line for permanently detaching its rear part which has a fitting device attachable to a corresponding part of the needle holder. The detached rear part of the plunger rod can be engaged with the needle holder to perform a radial motion that breaks the needle which thereafter is received by a cavity in the rear part of the detached plunger rod. The said plunger rod is preferably dimensioned so that when it is engaged with the needle holder to perform the radial motion, the interior wall of the cavity will meet the needle as close as possible to its attachment point. The said detached plunger rod will have a rear end with a handle part, an opening and a cavity formed of a rear part, a conical part and a cylindrical or slightly conical part. Close to the said opening there can be provided radial inwardly directed knobs which can be fitted to a corresponding neck part of the needle holder. The rear part of the plunger rod has now become a common rigid needle shield which can protect the user from accidental needle sticks.

In an especially preferred embodiment of the present invention the distance between the fitting device or the knobs of the detached hollow plunger rod and the point where the conically formed cavity is converted to a cylindrical or slightly conical cavity and the distance between the corresponding neck part of the needle holder and the attachment point of the needle to the needle holder, are made substantially, or to the largest possible extent, the same.

Another object of the present invention is to provide a method for making an injection syringe non-reusable after injection by breaking its movable, and hollow, plunger rod with a radial motion along a pre-determined rupture line to permanently detach its rear part, engaging the said detached rear part of the plunger rod with the needle holder and thereby breaking the needle with a radial motion, before attacking the said rear part containing the broken needle to the needle holder. To perform such a method, the rear part of the plunger rod is engaged to the needle holder by a fitting device when breaking the needle and attaching the rear part of the plunger rod.

DETAILED DESCRIPTION OF THE INVENTION

Figure 3A:
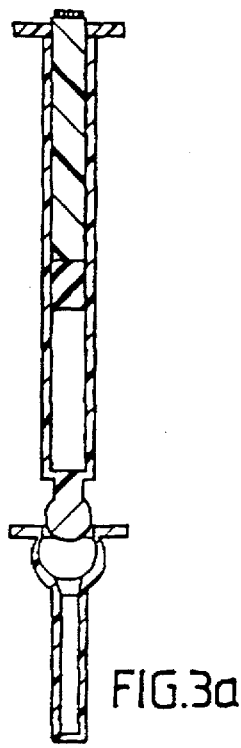

FIG. 3a schematically shows a syringe according to the present invention where the rear part of the plunger rod is detached and engaged with the needle holder before breaking the needle.

Figure 3B:
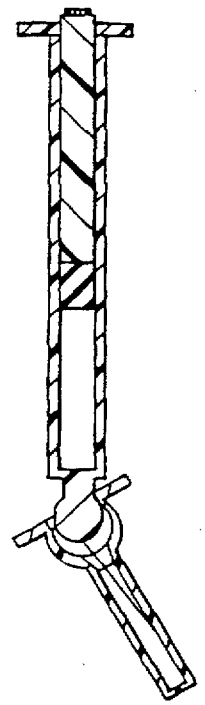

FIG. 3b shows the radial motion to break the needle with detached plunger rod engaged to the needle holder.

Figure 4:
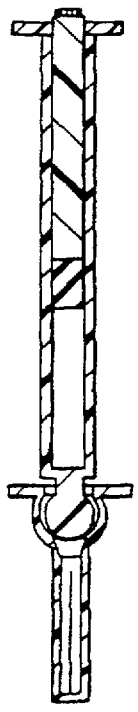

FIG. 4 shows the syringe ready for disposal with the hollow plunger rod, containing the broken needle, attached to the needle holder.

FIGS. 5a, 5b and 5c show the breaking of the needle and the attachment of the plunger rod in a more detailed manner.

Figure 1A:
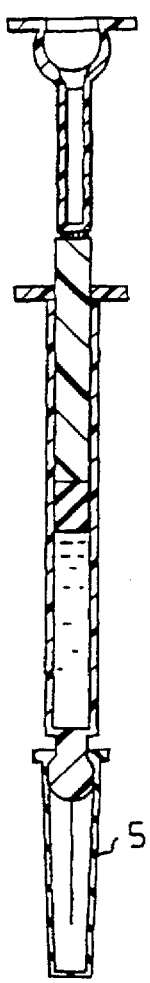
FIG. 1a shows a syringe according to the present invention as delivered from the manufacturer with a disposable rubber shield covering the needle.
Figure 1B:
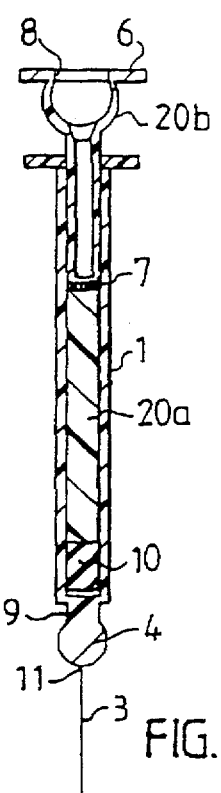
FIG. 1b shows a syringe according to the invention immediately after the administration of its contents.

Now referring to FIG. 1a and 1b showing a syringe according to the present invention comprising a syringe barrel (1) with a front part provided with a needle (3) attached to a needle holder (4), and a rear part sealed by a plunger (10) connected to a plunger rod (20a, 20b) that is axially slidable inside said barrel. The barrel (1) contains a certain amount of a liquid drug and preferably is prefilled with a single dosage of the drug before its assembly with the plunger. In certain other applications the drug can be provided in several dosages, and it can be contained in a cartridge having one or several compartments which subsequently, just prior to the administration, can be combined to a mixing compartment by a predetermined movement of the plunger rod.

The axially slidable plunger will, by its forward motion, exert a pressure on the liquid drug which thereby will be expelled through the needle into the patient. The needle (3) is preferably fixed to the needle holder (4) of the syringe barrel in a conventional manner, but other constructions with removable needles are also conceivable. The front part of the plunger rod (20a), also of a conventional type, is connected to the plunger (10) sealing the rear end of the syringe barrel and may optionally be connected to means for actuating the drug cartridge, which will not be further discussed here. The rear part of the plunger rod (20b) is shaped with a cavity to provide it with hollow structure which can receive both the needle (3) and the needle holder. The rear end of the plunger rod (20b) is constructed as a handle part (6) by means of which the plunger (10) is moved forwards into the barrel. The plunger rod (20a, 20b) can optionally be provided with means for stopping its forward motion after the dosage is expelled, such as an annular collar, or alternatively it may be equipped with some indication means, showing its end position.

Figure 2A:
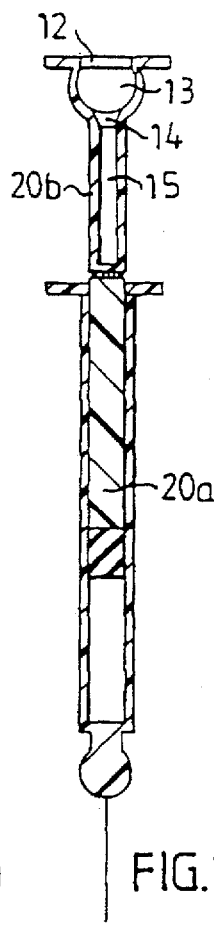
FIGS. 2a and 2b shows the syringe with the plunger rod in a position where it can be broken in two pieces along a rupture line with a simple radial motion.
Figure 2B:
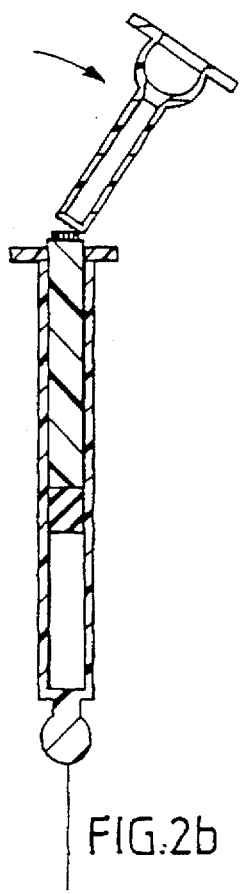

It is an important feature of the invention that the plunger rod (20a, 20b) is provided with a rupture line (7), along which it can be easily broken in two parts by the user by performing a simple radial motion. The rupture line is formed in the plunger material by conventional means during its manufacture in the injection moulding tools. It is important that the rupture line is formed in such a manner and in such a postion on the plunger rod (20a, 20b) so the syringe becomes irreversibly unusable because of its breaking into two parts, as shown in FIGS. 2a and 2b.

The detached rear part of the plunger rod (20b) will thereafter be engaged with the needle holder (4), as shown by the FIGS. 3a and 3b, in a position where it can break the needle at the attachment point to the needle holder (11), by turning the engaged plunger rod in a radial motion so the needle is forced against the interior walls of the hollow detached plunger rod. This position is also shown in FIGS. 5a and 5b, where it is demonstrated how the rear end (6) of the hollow plunger rod (20b) has an opening (12) to a cavity (13, 14, 15) fitting both the needle holder and the needle.

Close to the said opening (12) of the rear end the plunger rod (20b), which may formed as a slightly inawardly directed collar, there will be provided at least one inwardly directed fitting device (8) for engagement with the needle holder (4) in a predetermined manner. To facilitate the engagement of the broken plunger rod with the needle holder (4) and the breaking of the needle, the needle holder can be provided with some suitable corresponding engaging devices (not shown) like grooves, recesses or other devices, well-known to the person skilled in the art. In order to increase its flexibility, the rear end (6) of the detached plunger rod (20b) can have axially directed slits (not shown) distributed around its periphery.

After performing the breaking of the needle, the rear end (6) of the hollow plunger rod (20b), containing the needle in its cavity (13, 14, 15), is fitted around the needle holder (4) by positioning the fitting device (8) around the neck part (9) of the needle holder. The attached rear part of the plunger rod has now become a common rigid needle shield which can protect the user from accidental needle sticks. It is also possible to use the detached part as cover for the unbroken needle if the step of breaking the needle for some reason is not performed.

The fitting device (8) between the rear end (6) of the hollow plunger rod preferably consists of radial inwardly directed, if desired resilient, knobs distributed around the inner periphery of the hollow plunger rod, where said knobs fit snugly around the neck (9) which in turn preferably is adapted to fit said knobs by similar recesses. Other types of suitable fitting devices can also be used as alternatives within the scope of the present invention.

The needle holder is now contained in the cavity (13) of the detached plunger rod. This is shown in FIGS. 4 and 5c. Additional fitting means in the form of annular flanges/recesses, snap-lock devices or devices that permanently locks the said parts (20b) and (4) together are conceivable, but are not further described here, since they are well-known to each person skilled in this art.

The broken needle is now received by the hollow interior of the rear part of the plunger rod, which in its position fitted to the needle holder will act as a housing for needle when the entire syringe is disposed.

The cavity of the detached plunger rod (20b) is divided into a rear part (13) with a shape designed to fit the needle holder (4), a conical part (14) converted to a cylindrical or slightly conical part (15) designed to contain both the attached unbroken needle, as well as the broken needle.

It is of considerable importance that the above described parts of the syringe are designed to provide a convenient breaking procedure. The needle cover in the form of the hollow plunger rod (20b) shall thus be dimensioned so that its interior wall meets the needle as dose as possible to its attachment point (11). This requirement is fulfilled when, referring to FIGS. 5a and 5b, the distance a between the point A of the fitting device (8) of the detached hollow plunger rod (20b) and point C, where the conically formed cavity (14) is converted to a cylindrical cavity (15), and the distance b between the point B on the corresponding neck part (9) of the needle holder and the attachment point D or (11) of the needle to the needle holder, are made substantially or to the largest possible extent the same.

The barrel of the syringe can be made of glass or a conventional sterilisable polymer material, such as polypropylene. Polypropylene is also suitable material for the plunger which preferably shall be made from flexible material with a certain stiffness.

When using the syringe according to the present invention, an immediately disposable rubber shield (5) that protects the needle during storage, must initially be removed, see FIG. 1a. The needle can thereafter be positioned into the patient and the injection can be performed in accordance with what has been described above. After the administration of the drug is finished and the syringe is removed from the patient, the plunger rod can immediately be broken as described and its rear part can be engaged with the needle holder to perform a radial motion to break the needle which will be received by the housing formed of the hollow rear part of the plunger. The now unusable syringe may thereafter be disposed with ordinary domestic refusals without the risk of accidental needle sticks.

The person skilled in the art may easily find alternative features to those described herein that will have a similar function and still be contained within the general protective scope of this invention as it is presented by the following claims.

We claim:

1. A drug containing non-reusable injection syringe with a hollow plunger rod (20a, 20b) connected to a plunger (10) movable in the barrel (1) for injecting the drug through the needle (3), said syringe having a cover (20b) attachable to the needle holder (4) to protect the needle after injection, wherein said plunger rod is provided with a rupture line (7) for permanently detaching its hollow rear part (20b) characterized in that said hollow detached rear part of the plunger rod (20b) is dimensioned so that when it is engaged with the needle holder (4) to perform a radial motion, the interior wall of its cavity (13, 14, 15) will meet the needle as close as possible to its attachment point (11) in order to break the needle, which is received by said cavity (13, 14, 15) of said plunger rod, which thereafter, by means of a fitting device (8), is attached to a corresponding part (9) of the needle holder to form a cover for the inoperative contaminated needle.

2. A syringe according to claim 1 characterized that the detachable part of the plunger has a rear end with a handle part (6) having an opening (12) and a cavity formed of a rear part (13), a conical part (14), a cylindrical or slightly conical part (15), and radial inwardly directed knobs (8) which can be fitted with a corresponding neck part (9) of the needle holder.

3. A syringe according to claim 2 characterized in that the distance a between the point A of the fitting device (8) of the detached hollow plunger rod (20b) and point C, where the conically formed cavity (14) is converted to a cylindrical or slightly conical cavity (15), and the distance b between the point B on the neck part (9) of the needle holder corresponding to the device (8) and the attachment point D or (11) of the needle to the needle holder, are made substantially the same.

4. A syringe according to any of claims 1 characterized in that the rupture line is placed in such a position on the plunger so it will be impossible to use the syringe for injection after its breakage.

5. A method for making a injection syringe non-reusable after injection characterized by breaking its movable and partially hollow plunger rod (20a, 20b) along a predetermined rupture line (7) for permanently detaching its rear part (20b), engaging the said detached rear part of the plunger with the needle holder (4) and breaking the needle (3) with a radial motion, before attaching said rear part containing the broken needle to the needle holder.

6. A method according to claim 5 characterized in that the rear part of the plunger and the needle holder is engaged by fittings (8), (9) when breaking the needle and attaching the rear part of plunger rod (20b).

7. A non-reusable injection syringe having a barrel and a hollow plunger rod connected to a plunger which is moveable in the barrel, said syringe having a needle cover attachable to a needle holder of the syringe within which cover a detached needle is contained, said needle cover being provided with a fitting device which is attached to a corresponding part of the needle holder, thereby forming a container for the detached needle.

8. A syringe according to claim 7, wherein the hollow plunger rod and needle cover have ends which correspond to a common rupture line.

* * * * *